United States Patent [19]
Applegate

[11] 4,166,460
[45] Sep. 4, 1979

[54] ANKLE PROTECTOR

[75] Inventor: Leslie T. Applegate, Cincinnati, Ohio

[73] Assignee: Surgical Appliance Industries, Inc., Cincinnati, Ohio

[21] Appl. No.: 834,443

[22] Filed: Sep. 19, 1977

[51] Int. Cl.² ............................................. A61F 3/00
[52] U.S. Cl. .................................. 128/80 H; 128/166
[58] Field of Search ............... 128/80 R, 80 F, 80 E, 128/80 H, 87 R, 165, 166

[56] References Cited
U.S. PATENT DOCUMENTS

| | | | |
|---|---|---|---|
| 674,066 | 5/1901 | Mitchell | 128/166 |
| 911,243 | 2/1909 | Johannesen | 128/80 F |
| 932,177 | 8/1909 | Roth | 128/80 F |
| 1,847,823 | 3/1932 | Dresser | 128/80 F |
| 1,858,162 | 5/1932 | MacNamee | 128/165 |
| 3,073,305 | 1/1963 | Biggs, Jr. et al. | 128/166 |
| 3,805,773 | 4/1974 | Sichau | 128/80 E |

FOREIGN PATENT DOCUMENTS 948372  6/1949  France ................................. 128/80 F Primary Examiner—John D. Yasko
Attorney, Agent, or Firm—Wood, Herron & Evans

[57] ABSTRACT

An ankle protector for inhibiting lateral ankle bending motion assoicated with strains including an elastic stocking dimensioned and configured to snugly embrace the instep, heel, and ankle of the wearer; a semi-rigid heel cup positioned within the stocking in the heel region thereof, which is dimensioned and configured to snugly embrace the heel of the user; and a pair of elongated stays secured to opposite sides of the stocking which have their lower ends pinned to opposite sides of the heel cup to facilitate pivotal motion thereof with respect to the heel cup only about an axis parallel to the axis about which the ankle flexes in normal walking or running activity. To enhance the lateral support, a pair of straps are provided, each having one end secured to the bottom of the stocking, which are adapted to encircle the instep and ankle of the wearer in criss-cross fashion. Velcro fastening means at the free ends of the straps secure them to a cooperating Velcro pad fixed to the upper portion of the stocking. The upper edge of the stocking is turned down over the Velcro fastening assembly to conceal and promote security of the fastened straps.

7 Claims, 6 Drawing Figures

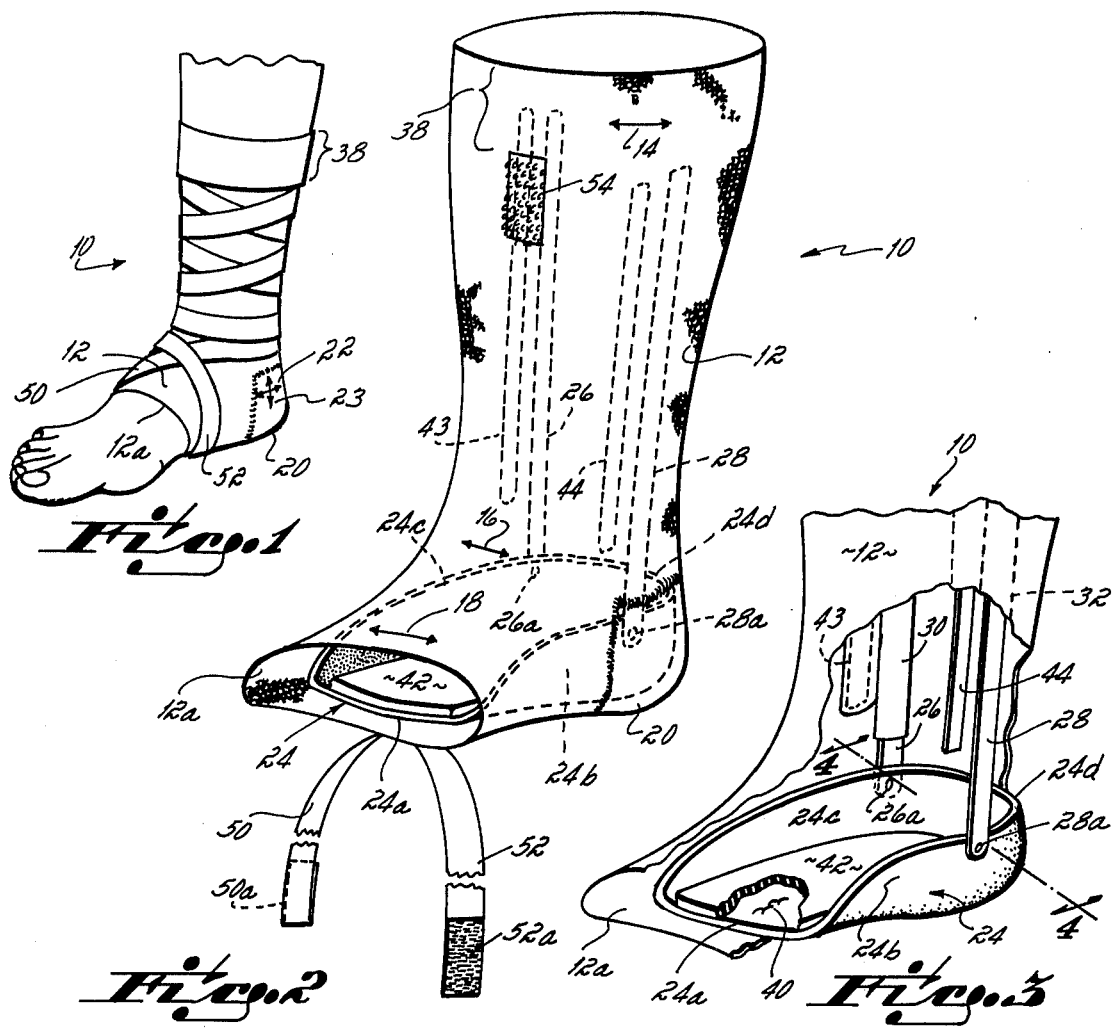
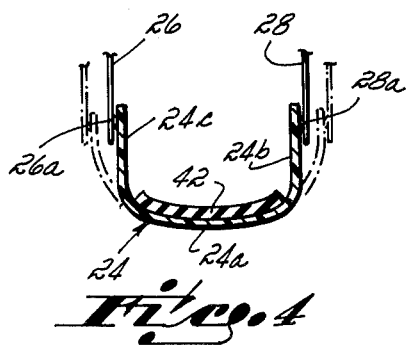
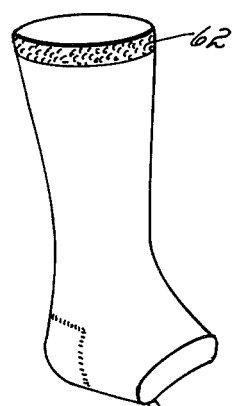
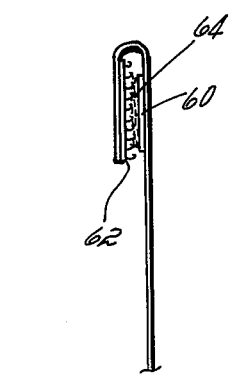

ANKLE PROTECTOR

This invention relates to an ankle protector and more particularly to an ankle protector for providing lateral support to the ankle and thereby minimizing the likelihood of movement of the ankle in a manner associated with a sprain.

Sprained ankles are common among athletes, even those possessing normal, healthy ankles. Sprained ankles are even more common among those whose ankles are weak by reason of either previous sprains or some other ligament or muscle deficiency. To minimize the likelihood that the ankle will become sprained, it has been found desirable to provide an ankle support device which tends to immobilize the ankle against movement in a direction other than that normally encountered in the course of walking or running. While various schemes have been proposed for providing lateral support to the ankle, the proposals leave considerable room for improvement.

For example, many ankle supports are time consuming and/or difficult to put on and take off. Others are uncomfortable. Some unduly restrict movement of the ankle and, hence, impede normal ankle flexing encountered during walking and running. Still others are difficult to clean by reason of their design and/or the materials used. Some are far too bulky, and others provide inadequate support against sprains.

Accordingly, it has been an objective of this invention to provide a lightweight, readily cleaned, and inexpensive brace which is easy to put on and take off, and yet one which provides substantial support for the ankle without being uncomfortable. The foregoing objective has been accomplished in the preferred embodiment of the invention by providing an elastic stocking configured and dimensioned to encircle the heel, ankle and instep of the wearer, a semi-rigid heel cup located within the stocking in the heel region thereof which is dimensioned and configured to snugly embrace the user's heel, a pair of semi-rigid stays secured in vertical disposition to opposite sides of the portion of the stocking which engages the wearer's ankle and the leg portion thereabove, and means for securing the stays at their lower ends to opposite side walls of the heel cup to facilitate pivotal motion thereof about an axis parallel to the normal bending axis of the ankle encountered during normal walking and running motion. The foregoing construction provides lateral support to the ankle to stabilize it against flexing motion about an axis other than that encountered during normal walking and running motion, thereby minimizing the likelihood of sprains.

In accordance with a further aspect of the invention, designed to provide additional ankle stabilization and support, at least one strap, preferably two, are anchored at one end to the bottom of the stocking for wrapping the instep and ankle. The strap(s) which have a length sufficient to facilitate multiple wraps about the ankle region, have Velcro fastening means at the free ends thereof for adjustably securing the straps to the stocking proximate its upper edge. To conceal the fastening means and enhance the fastening action of the Velcro, the upper edge of the stocking is turned down to overlie the fastened straps.

The elastic stocking, which in a preferred form is located outboard of the pivotally connected stays, and the straps which are also located outward of the stays, combine to urge the stays inwardly against the lower portion of the leg located above the ankle over substantially the entire length of the stays, thereby maintaining the stays in intimate contact with the lower leg of the wearer. This, coupled with the fact that the stays at the lower end are pivotally connected to the heel cup such that only pivoting action about an axis parallel to that encountered during normal walking is permitted, provides a substantial degree of lateral support to the ankle to inhibit sprains.

These and other features, advantages, and objectives of the invention will be more readily apparent from a detailed description thereof taken in conjunction with the drawings in which:

FIG. 1 is a perspective view of one embodiment of the ankle protector of this invention showing it in place on the wear's ankle as it would be worn in use;

FIG. 2 is a perspective view of the ankle protector of FIG. 1 as it would appear prior to placement on the ankle of the user;

FIG. 3 is a perspective view, partially cut away, of a portion of the ankle protector of FIG. 1 showing the inner heel plate and the lateral stays hinged thereto;

FIG. 4 is a cross-sectional view taken along line 4—4 of FIG. 3 showing the side walls of the plastic heel cup in different lateral positions dependent upon the size of the heel located therein;

FIG. 5 is a perspective view of another embodiment of the invention in which the Velcro fastening means extends circumferentially immediately adjacent the upper edge of the ankle section of the stocking; and FIG. 6 is a vertical cross-sectional view of the embodiment of FIG. 5 showing the circumferential Velcro-bearing edge of the ankle section of the stocking turned down over the strap to secure it.

With reference to FIGS. 1-3, the ankle protector 10 of this invention is seen to include an elastic stocking 12 which, except for the toe region which is omitted, is shaped generally in the form of an ankle length sock. While the toe region of the stocking 12 has been omitted for purposes of comfort and convenience, it could have been included. The stocking 12, to maximize support for the ankle, particularly lateral support, and yet minimize any discomfort to the wearer, is preferably elasticized, that is, stretchable, only in a circumferential direction as indicated by double headed arrows 14, 16 and 18, except in the region of the heel where an elastic insert 20 stretchable in both a horizontal and a vertical direction, as indicated by arrows 22 and 23, is provided. Also possible is the use of two-way stretch elastic for the entire stocking 12.

To provide lateral support, a plastic heel cup 24 is provided in combination with a pair of vertical stays 26 and 28. The plastic heel cup 24 preferably is semi-rigid to maximize support without seriously reducing heel comfort. With some sacrifice in comfort and adaptability in fit a rigid heel cup could be used. The heel cup 24 includes a bottom section 24a, opposite side walls 24b and 24c extending vertically upwardly from opposite sides of the bottom 24a, and a rear wall 24d extending vertically upwardly from the rear edge of the bottom 24a. The bottom, sides, and rear walls 24a, 24b, 24c and 24d of the plastic heel cup 24 are preferably integrally formed, such as, by injection molding. Stays 26 and 28 at their lower end are hingedly connected to the upper margin of the side walls 24c and 24b by pins 26a and 28a. The stays 26 and 28, for substantially their entire length, are positioned within vertically disposed pockets 30 and 32 formed on the inner side wall portions of the stocking 12. The pockets 30 and 32 are preferably formed by stitching an inelastic fabric strip to the inside of the stocking. When a pocket is formed in this manner, the stays 26 and 28 lie between confronting surfaces of the stocking and inelastic strip stitched thereto. Preferably, the stays 26 and 28 and their associated pockets 30 and 32 extend upwardly for a substantial distance, but not above an upper marginal region generally indicated by the reference numeral 38 which, for reasons to become more apparent hereafter, is designed to be folded downwardly when the stocking is worn. The point at which the lower ends of the stays 26 and 28 are connected by pins 26a and 28a to the heel cup side wall 24c and 24b is selected to maximize comfort when the foot is bent in the normal cause of walking with the ankle protector in place on the wearer's ankle.

The plastic heel cup 24 is preferably anchored to the bottom 12a of the stocking 12 by any suitable means such as stitching 40. In addition, and to maximize comfort when the ankle protector is worn, a soft resilient pad 42, for example, fabricated of foam rubber, is provided as a liner for the bottom surface 24a of the plastic heel cup 24. If desired, the stitching 40 which secures the plastic heel cup 24 to the stocking bottom 12a can also pass through the foam pad 40 to anchor it in place with respect to the plastic heel cup 24.

The stays 26, 28 are preferably fabricated of semi-rigid material. A form of construction for the stays 26 and 28 found satisfactory is that disclosed in U.S. Pat. No. 3,298,365 assigned to the assignee of this invention.

To enhance the support provided by the stocking 12, additional stays 43 and 44, which are not hinged to the plastic heel cup 24, may be provided. These stays 43 and 44, like the stays 26 and 28, can be fabricated of semi-rigid material and located within a pocket formed on the interior of the stocking. Preferably, the stays 43 and 44 are disposed parallel to the stays 26 and 28, but terminate a short distance above the upper edge of the plastic heel side walls 24b and 24c.

Since the stays 26 and 28 can pivot with respect to the plastic heel cup 24 only about an axis parallel to the axis through which the ankle bends during normal walking or running motion, lateral support to the ankle joint is provided, inhibiting inward and outward bending of the ankle in a direction normally associated with a sprained ankle.

To enhance the support provided by the ankle protector 10, a pair of inelastic straps 50 and 52, which can be wrapped around the ankle and secured in place in a manner to be described, are provided. The straps 50 and 52 are sized to permit multiple encirclement of the instep and ankle and will have varying lengths depending upon the size of the ankle protector. For an ankle protector sized for use by an adult, a length of 3½ feet for each of the straps 50 and 52 has been found satisfactory. The straps 50 and 52 preferably are anchored by suitable stitching to the central bottom portion of the ankle protector at a point approximately underlying the instep. To enhance the anchoring of the inner ends of the straps 50 and 52 to the bottom of the stocking 12, the means utilized to anchor the straps, such as stitching 40, can also pass through the bottom 24a of the plastic heel cup 24. In this way, the ends of the straps 50 and 52 are secured to both the bottom section 12a of the stocking 12 and the bottom 24a of the plastic heel cup 24.

As is clear from FIG. 1, the straps 50 and 52 are designed to encircle, in criss-cross fashion, the instep and ankle of the wearer with the free ends anchored below the upper marginal stocking region 38. To facilitate anchoring the outer free ends of the straps 50 and 52, Velcro strips 50a and 52a are secured to the straps 50 and 52 at the outer or free ends thereof. Cooperating with the Velcro sections 50a and 52a of the straps 50 and 52 is a Velcro strip 54 secured to the outer surface of the front of the stocking 12 at a point below the upper marginal region 38.

After the straps 50 and 52 have been encircled about the ankle in criss-cross fashion, Velcro sections 50a and 52a thereof are impressed against the Velcro pad 54. This anchors the free ends of the straps 50 and 52 to the upper front portion of the stocking 12, as well as anchoring the straps with respect to each other. To facilitate anchoring the straps 50 and 52 about ankles of wearers having varying ankle dimensions in a circumferential direction, the Velcro sections 50a and 52a preferably have a length of approximately 3–5 inches measured in the longitudinal direction of the straps 50 and 52. This enables the straps 50 and 52 to be anchored to the Velcro section 54 at varying distances from the free ends thereof.

To enhance the anchoring of the Velcro sections 50a and 52a of straps 50 and 52 to the Velcro section 54 secured to the front of the stocking 12, the upper marginal region 38 of the stocking is rolled down over the free ends of the straps 50 and 52 after the Velcro sections 50a and 52a thereof have been secured to the Velcro section 54. With the upper marginal region 38 rolled down over the fastened Velcro sections 50a, 52a and 54, inward radial forces are applied to the Velcro sections 50a and 52a in a direction urging them into contact with the Velcro pad 54 secured to the front of the stocking 12. This not only promotes secure fastening of the straps 50 and 52, but also protects the uppermost portions of the straps 50 and 52 from snagging on some stationary object and becoming loosened, or sliding up over the top of the stocking to bear directly against the leg of the wearer which, if it occurred, could become a source of discomfort. It also conceals the Velcro fasteners.

While the plastic heel cup 24 is semi-rigid in a preferred form, it nevertheless deforms laterally to accommodate different sized heels. With reference to FIG. 4, the solid line position of the plastic heel cup 24 shows the side wall section thereof in an inner position to accommodate a relatively small size heel, while the dotted line position shows the side walls of the heel cup deflected outwardly to accommodate a large size heel.

In accordance with a second embodiment of the invention shown in FIGS. 5 and 6, only a single strap 60 is provided. The strap 60 is secured at its inner end to the bottom of the stocking in much the same fashion as the straps 50 and 52 of the embodiment of FIGS. 1–3. In the embodiment of FIGS. 5 and 6, however, a circumferential Velcro strip 62 located immediately adjacent the upper edge of the ankle section of the stocking is provided. As shown in FIG. 6, a Velcro strip 64 secured to the free end of the single strap 60 with its active surface directed outboard is designed to engage the inwardly directed active surface of Velcro strip 62 when the upper edge of the ankle section of the stocking is turned down as shown in FIG. 6. By turning down the upper edge of the ankle section of the stocking, not only is the fastening action of the cooperating Velcro fasteners 62 and 64 enhanced, but the Velcro fastener is concealed from view as it is in the embodiment of FIGS. 1-3.

What is claimed is:

1. An ankle protector comprising:
   a sleeve having ankle and heel sections dimensioned and configured to snugly encircle at least the ankle and heel of a wearer, said sleeve being elastic in at least a circumferential direction,
   first and second semi-rigid stays secured to opposite sides of said ankle section, said stays being disposed generally parallel to the longitudinal axis of said ankle section, said stays each having upper and lower ends,
   a heel cup exhibiting semi-rigid characteristics having a bottom and opposite side walls to receive the heel of a wearer, said opposite side walls being dimensioned and configured to snugly embrace substantially the entirety of the sides of the wearer's heel, said heel cup being disposed within said heel section of said sleeve,
   means connecting the lower end of each of said stays to a different one of said opposite side walls of said heel cup for pivotal movement about an axis parallel to the normal flexure axis of a wearer's ankle encountered during walking, thereby facilitating comfortable walking action while inhibiting undesirable lateral ankle motion associated with a sprain.

2. The ankle protector of claim 1 further including fastener means to secure said heel cup to said sleeve heel section.

3. The ankle protector of claim 1 further comprising:
   at least one strap having first and second ends, said first end being secured to said sleeve, said strap having a length dimensioned to encircle said ankle a plurality of times, a strap fastener secured to said sleeve at a distance from the upper edge of the ankle section thereof sufficient to permit said upper edge to be turned down over said fastener and thereby conceal said fastener and enhance the fastening action of said fastener when said strap is wrapped around the wearer's ankle with its second end secured by said fastener.

4. The ankle protector of claim 3 including:
   at least two straps each having a first end secured to said sleeve and a length dimensioned to encircle said ankle multiple times,
   Velcro strips secured to said second ends of said straps, and
   wherein said fastener is a Velcro pad for fastening said second ends of said straps to said sleeve.

5. The ankle protector of claim 4 wherein said first ends of said straps are fastened to said sleeve at approximately a common point on the bottom of said heel section, and wherein said Velcro pad is secured to the front of said ankle section.

6. The ankle protector of claim 1 further comprising a strap having a first end secured to said sleeve and a second end provided with Velcro, said strap having a length dimensioned to encircle said ankle multiple times,
   a Velcro strip disposed circumferentially about the upper edge of said ankle section to secure said second end of said strap when said Velcro-bearing edge of said ankle section is turned down in overlying relationship to said Velcro-bearing end of said strap.

7. The ankle protector of claim 1 wherein said opposite side walls of said heel cup bend outwardly to comfortably accommodate different size heels inserted therein.

* * * * *